US012599395B2

(12) United States Patent
Kroll et al.

(10) Patent No.: US 12,599,395 B2
(45) Date of Patent: Apr. 14, 2026

(54) SURGICAL FORCEPS AND FIXATION THEREOF

(71) Applicant: GYRUS ACMI, INC, Westborough, MA (US)

(72) Inventors: Mark J. Kroll, Dresser, WI (US); Cole D. Halstead, Ramsey, MN (US); William E. Butler, Minneapolis, MN (US); John Mensch, Plymouth, MN (US); Theodore C. Blus, Arden Hills, MN (US); Robert D. Whitney, Fort Wayne, IN (US); Matthew J. Warzecha, Shorewood, MN (US)

(73) Assignee: Gyrus ACMI, Inc., Westborough, MA (US)

( * ) Notice: Subject to any disclaimer, the term of this patent is extended or adjusted under 35 U.S.C. 154(b) by 0 days.

(21) Appl. No.: 19/108,304

(22) PCT Filed: Sep. 12, 2024

(86) PCT No.: PCT/US2024/046441
§ 371 (c)(1),
(2) Date: Mar. 3, 2025

(87) PCT Pub. No.: WO2025/059340
PCT Pub. Date: Mar. 20, 2025

(65) Prior Publication Data
US 2026/0069303 A1      Mar. 12, 2026

Related U.S. Application Data

(60) Provisional application No. 63/582,090, filed on Sep. 12, 2023.

(51) Int. Cl.
*A61B 17/29* (2006.01)
*A61B 17/295* (2006.01)
*A61B 18/14* (2006.01)

(52) U.S. Cl.
CPC .. *A61B 17/2909* (2013.01); *A61B 2017/2901* (2013.01); *A61B 2017/2903* (2013.01);
(Continued)

(58) Field of Classification Search
CPC ... A61B 17/29; A61B 17/2909; A61B 17/295; A61B 18/1445; A61B 2017/2901;
(Continued)

(56) References Cited

U.S. PATENT DOCUMENTS

| 8,469,992 | B2 | 6/2013 | Roy et al. |
| 2007/0179499 | A1 | 8/2007 | Garrison |

(Continued)

FOREIGN PATENT DOCUMENTS

| WO | WO-2016148888 A1 | 9/2016 |

OTHER PUBLICATIONS

"International Application Serial No. PCT/US2024/046441, International Search Report mailed Dec. 13, 2024", 4 pgs.
(Continued)

*Primary Examiner* — Brooke Labranche
(74) *Attorney, Agent, or Firm* — Schwegman Lundberg & Woessner, P.A.

(57) ABSTRACT

A surgical forceps can include an outer shaft, a first jaw, a second jaw, and an inner shaft. The first jaw can include a first flange and a second flange. The first jaw can be pivotably coupled to the outer shaft. The second jaw can include a third flange and a fourth flange. The third flange can be welded to the outer shaft and the fourth flange can be welded to the outer shaft. The inner shaft can be engaged with the first flange and the second flange. The inner shaft can be movable with respect to the outer shaft, the third flange, and the fourth flange to move the first jaw between an open position and a closed position.

17 Claims, 6 Drawing Sheets

Distal

Proximal

(52) U.S. Cl.
CPC ................ *A61B 2017/2933* (2013.01); *A61B 2017/2946* (2013.01); *A61B 2017/2947* (2013.01); *A61B 17/295* (2013.01); *A61B 18/1445* (2013.01); *A61B 2018/1455* (2013.01)

(58) Field of Classification Search
CPC .... A61B 2017/2903; A61B 2017/2933; A61B 2017/2946; A61B 2017/2947; A61B 2018/1455
See application file for complete search history.

(56) References Cited

U.S. PATENT DOCUMENTS

| | | | |
|---|---|---|---|
| 2013/0296848 A1* | 11/2013 | Allen, IV | ............... A61B 17/29 606/41 |
| 2015/0297278 A1* | 10/2015 | Scheller | ................ A61B 17/29 606/41 |
| 2020/0305911 A1 | 10/2020 | Pham et al. | |
| 2021/0177495 A1 | 6/2021 | Ross et al. | |
| 2021/0244426 A1* | 8/2021 | Roomi | ................... A61B 17/29 |
| 2022/0015823 A1 | 1/2022 | Wilson et al. | |
| 2022/0287761 A1 | 9/2022 | Blus et al. | |
| 2023/0200888 A1 | 6/2023 | Fry et al. | |

OTHER PUBLICATIONS

"International Application Serial No. PCT/US2024/046441, Written Opinion mailed Dec. 13, 2024", 7 pgs.

* cited by examiner

Proximal

210

A1

A

208

218

212a

222b

222a

220b

216

214

200

224a

224b

206a

209a

206b

209b

202

Distal

SURGICAL FORCEPS AND FIXATION THEREOF

PRIORITY CLAIM

This application is a U.S. National Stage filing under 37 U.S.C. § 371 from International Application No. PCT/US2024/046441, filed Sep. 12, 2024, which claims the benefit of priority to U.S. Provisional Patent Application Ser. No. 63/582,090, filed Sep. 12, 2023, the contents of which are hereby incorporated by reference.

BACKGROUND

Medical devices for diagnosis and treatment, such as forceps, are often used for medical procedures such as laparoscopic and open surgeries. Forceps can be used to manipulate, engage, grasp, or otherwise affect an anatomical feature, such as a vessel or other tissue of a patient during the procedure. Forceps often include an end effector that is manipulatable from a handle of the forceps. For example, jaws located at a distal end of a forceps can be actuated via elements of the handle between open and closed positions to thereby engage the vessel or other tissue. Forceps can include an extendable and retractable blade that can be extended distally between a pair of jaws to lacerate the tissue. The handle can also be capable of supplying an input energy, such as electromagnetic energy or ultrasound, to the end effector for sealing of the vessel or tissue during the procedure.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Electrosurgical forceps are often used for grasping and cutting tissue. Some forceps include dual acting jaws where both jaws move relative to each other and the shafts and some forceps include single acting jaws where only a single jaw moves relative to the other jaw and the shafts. With single acting jaw forceps, one jaw must be fixed relative to the fixed shaft (e.g., the outer shaft) while the moving jaw is connected to the moving shaft to allow the moving jaw to move with respect to the shafts while movement of the fixed jaw with respect to the shafts and the moving jaw is fixed or prevented (or limited). Securing the fixed jaw to the shaft can be relatively difficult due to the size of the components (configured to be inserted through a lumen of a scope or other device, such as a trocar). The present disclosure can help to address these issues by securing flanges of the fixed jaw to the outer shaft using one or more welds, such as laser welds. The welds can be located such that the welding operations can be performed from an external location following assembly of the components of the forceps, helping to simplify manufacturing while providing a rigid and secure connection between the fixed jaw and the fixed (e.g., outer) shaft or tube.

The above discussion is intended to provide an overview of subject matter of the present patent application. It is not intended to provide an exclusive or exhaustive explanation of the invention. The description below is included to provide further information about the present patent application.

Figure 1:
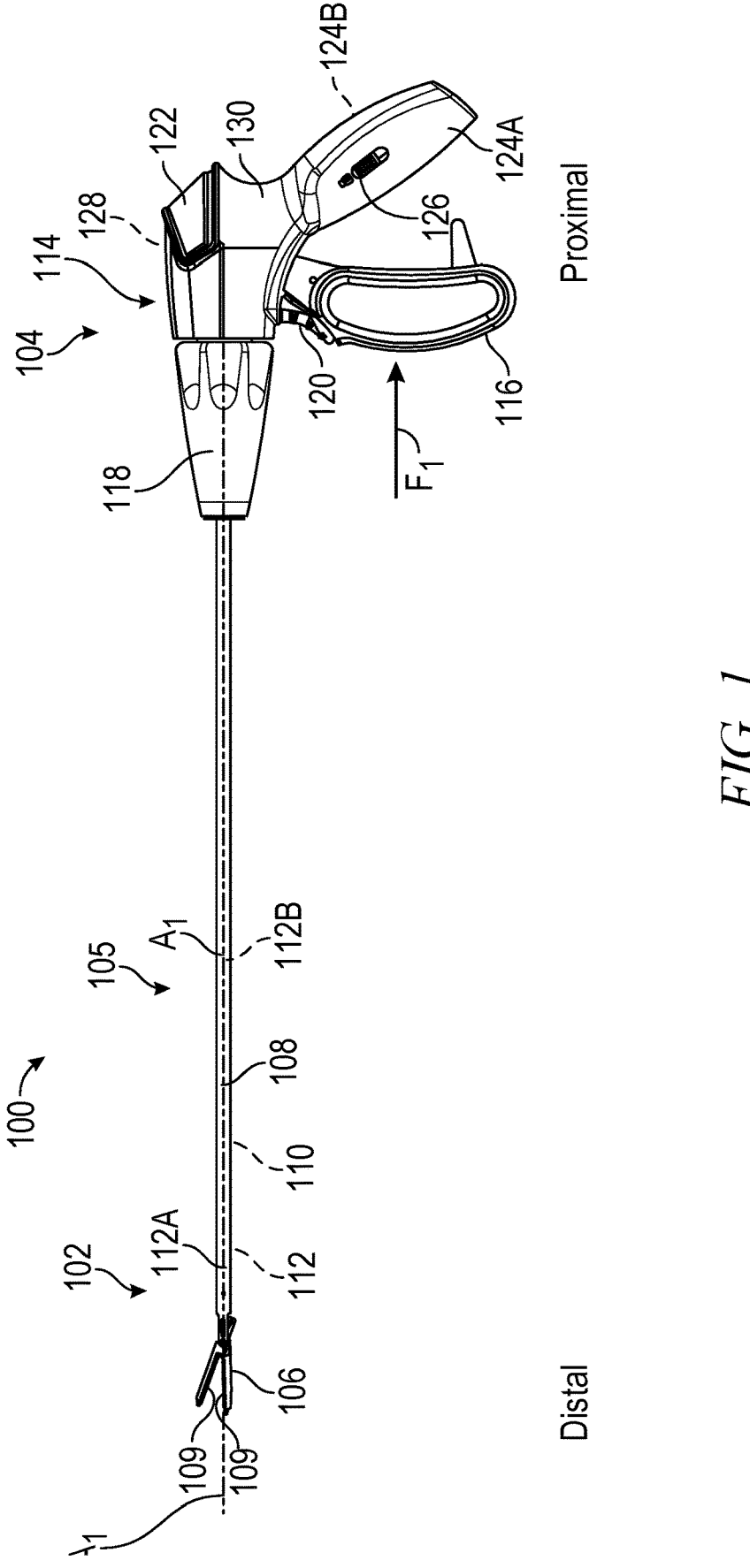
FIG. 1 illustrates a side view of a forceps showing jaws in an open position.

FIG. 1 illustrates a side view of a forceps 100 showing jaws in an open position. The forceps 100 can include an end effector 102, a handpiece 104, and an intermediate portion 105. The end effector 102 can include jaws 106 (including electrodes 109), an outer shaft 108, an inner shaft 110, and a blade assembly 112. The handpiece 104 can include a housing 114, a lever 116, a rotational actuator 118, a trigger 120, an activation button 122, a fixed handle 124a and 124b, and a handle locking mechanism 126. The housing 114 can include a first housing portion 128, and a second housing portion 130. FIG. 1 also shows orientation indicators Proximal and Distal and a longitudinal axis A1.

Generally, the handpiece 104 can be located at a proximal end of the forceps 100 and the end effector 102 can be located at the distal end of the forceps 100. The intermediate portion 105 can extend between the handpiece 104 and the end effector 102 to operably couple the handpiece 104 to the end effector 102. Various movements of the end effector 102 can be controlled by one or more actuation systems of the handpiece 104. For example, the end effector 102 can be rotated along the longitudinal axis A1 (FIG. 2) of the forceps 100. Also, the handpiece can operate the jaws 106, such as by moving one or more of the jaws 106 between open and closed positions. The handpiece 104 can also be used to operate the blade assembly 112 for cutting tissue and can operate the electrode 109 for applying electromagnetic energy to tissue. The end effector 102, or a portion of the end effector 102, can be one or more of: opened, closed, rotated, extended, retracted, and electromagnetically energized.

The housing 114 can be a frame that provides structural support between components of the forceps 100. The housing 114 is shown as housing at least a portion of the actuation systems associated with the handpiece 104 for actuating the end effector 102. However, some or all of the actuation components need not be housed within the housing 114. The housing 114 can provide a rigid structure for attachment of components, but the housing 114 does not necessarily house the components completely, or can house a portion of one or more of the components.

The drive shaft 110 can extend through the housing 114 and out of a distal end of the housing 114, or distally beyond housing 114. One or more of the jaws 106 can be connected to a distal end of the drive shaft 110. The outer shaft 108 can be a hollow tube positioned around the drive shaft 110. A distal end of the outer shaft 108 can be located adjacent the jaws 106. The distal ends of the drive shaft 110 and the outer shaft 108 can be rotationally locked to one or more of the jaws 106 (e.g., only to one jaw in an example where the end effector 102 includes single-acting jaws). The rotational actuator 118 can be positioned around the distal end of the housing 114. The outer shaft 108 can extend distally beyond the rotational actuator 118. The blade shaft 112b can extend through the drive shaft 110 and the outer shaft 108. A distal end of the blade shaft 112*b* can be located near the jaws 106. A proximal end of the blade shaft 112*b* can be within housing 114.

The handpiece 104 can enable a user to extend and retract a blade 112*a* of the blade assembly 112, which can be attached to a distal end of a blade shaft 112*b* of the blade assembly 112. In some examples, the blade 112*a* can extend an entirety of a length between the handle 104 and the end effector 102. In some examples, the handpiece 104 can include features that inhibit the blade assembly 112 from being extended until the jaws 106 are at least partially closed, or fully closed. The blade 112*a* can be extended by displacing the trigger 120 proximally and the blade 112*a* can be retracted by allowing the trigger 120 to return distally to a default position.

A proximal portion of the trigger 120 can be connected to the blade shaft 112*b* within the housing 114 and a distal portion of the trigger 120 can extend outside of the housing 114 adjacent to, and in some examples nested with, the lever 116 in the default or unactuated positions. The activation button 122 can be coupled to the housing 114 and can include or be connected to electronic circuitry within the housing 114. Such circuitry can send or transmit electromagnetic energy through forceps 100 to the jaws 106. In some examples, the electronic circuitry may reside outside the housing 114 but can be operably coupled to the housing 114 and the end effector 102.

In operation of the forceps 100, a user can displace the lever 116 proximally by applying a Force F1 to the lever 116 to actuate the drive shaft 110 to drive at least one of the jaws 106 from the open position (FIG. 3) to the closed position (FIG. 2), which can allow the user to clamp down on and compress a tissue. The handpiece 104 can also allow a user to rotate the rotational actuator 118 to cause the end effector 102 to rotate, such as by rotating both the drive shaft 26 and the outer shaft 28 together.

In some examples, with the tissue compressed, a user can depress the activation button 122 to cause an electromagnetic energy, or in some examples, ultrasound, to be delivered to the end effector 102, such as to the electrode 109 and to the tissue. Application of such energy can be used to seal or otherwise affect the tissue being clamped. In some examples, the electromagnetic energy can cause tissue to be coagulated, sealed, ablated, or can cause controlled necrosis. When desired, the trigger 120 can be moved to translate the blade assembly 112 distally such that the blade 112*a* can extend between the jaws 106 in order to cut the tissue within the jaws 106. Such a process can be repeated, as desired.

In some examples, the forceps 100, or other medical device, may not include all the features described or may include additional features and functions, and the operations may be performed in any order. The handpiece 104 can be used with a variety of other end effectors to perform other methods.

Figure 2:
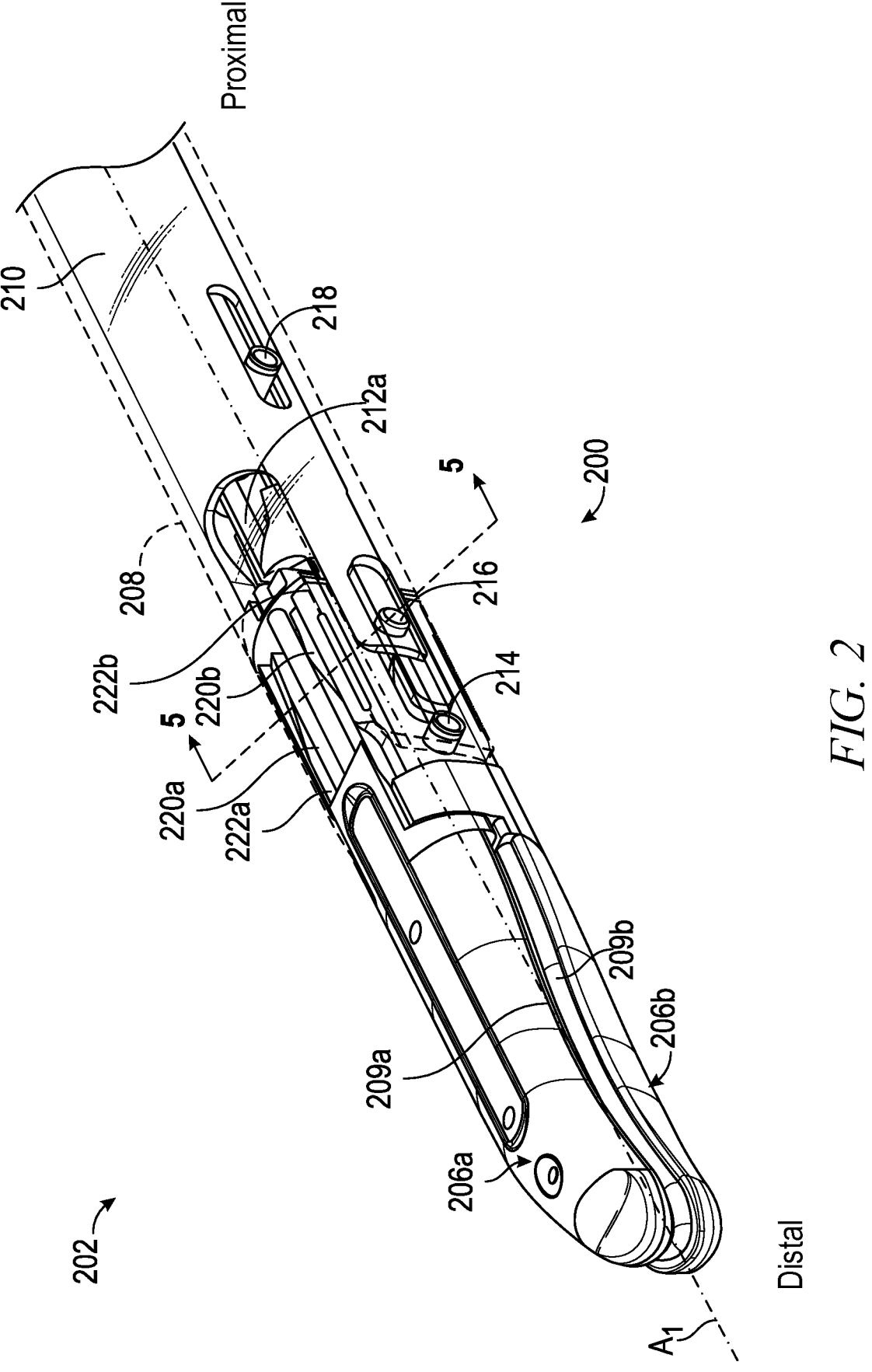
FIG. 2 illustrates an isometric view of a portion of forceps in a closed position.
Figure 3:
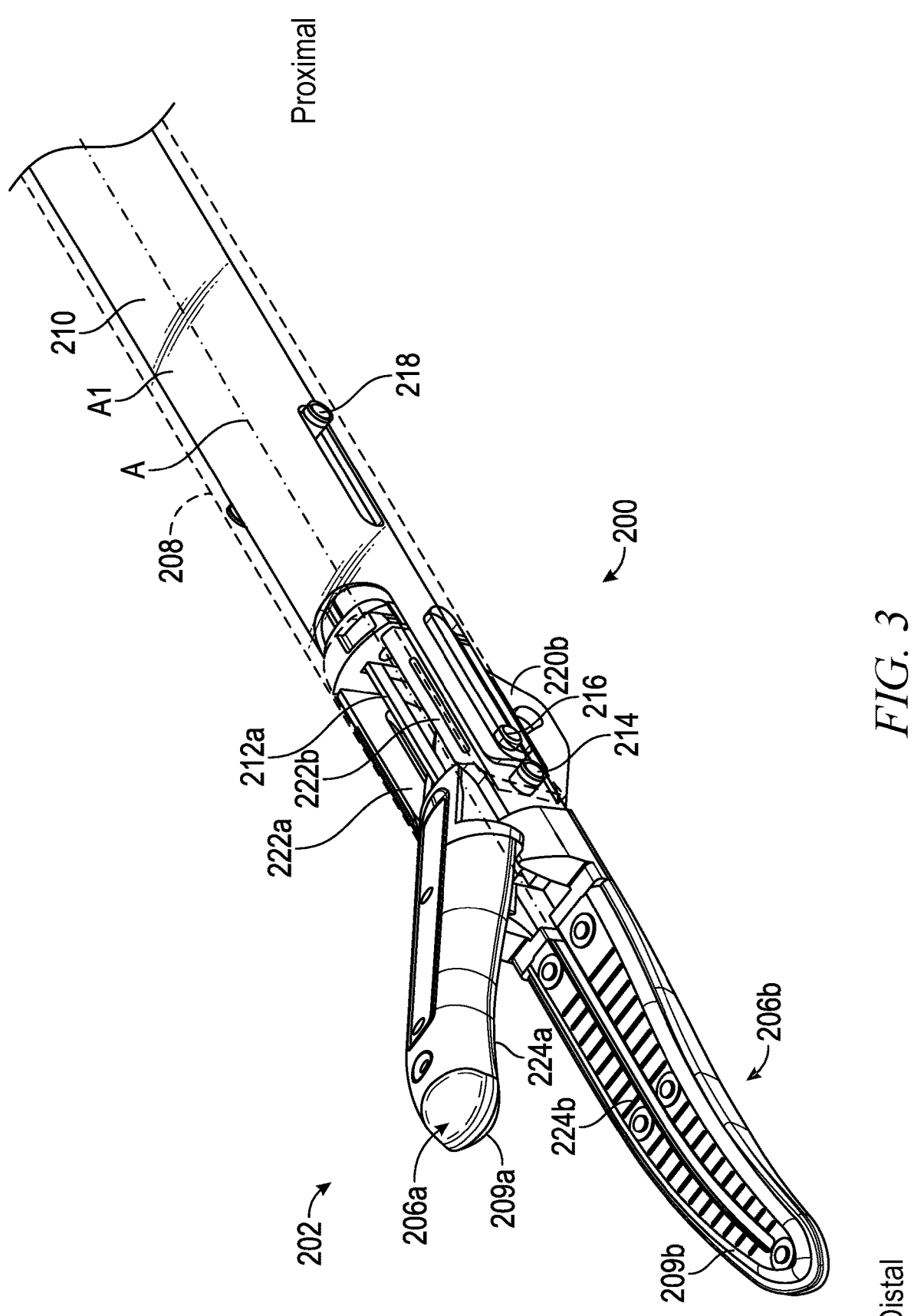
FIG. 3 illustrates an isometric view of a portion of forceps in an open position.

FIG. 2 illustrates an isometric view of a portion of forceps 200 in a closed position. FIG. 3 illustrates an isometric view of a portion of the forceps 200 in an open position. FIGS. 2-3 are discussed below concurrently.

Figure 5:
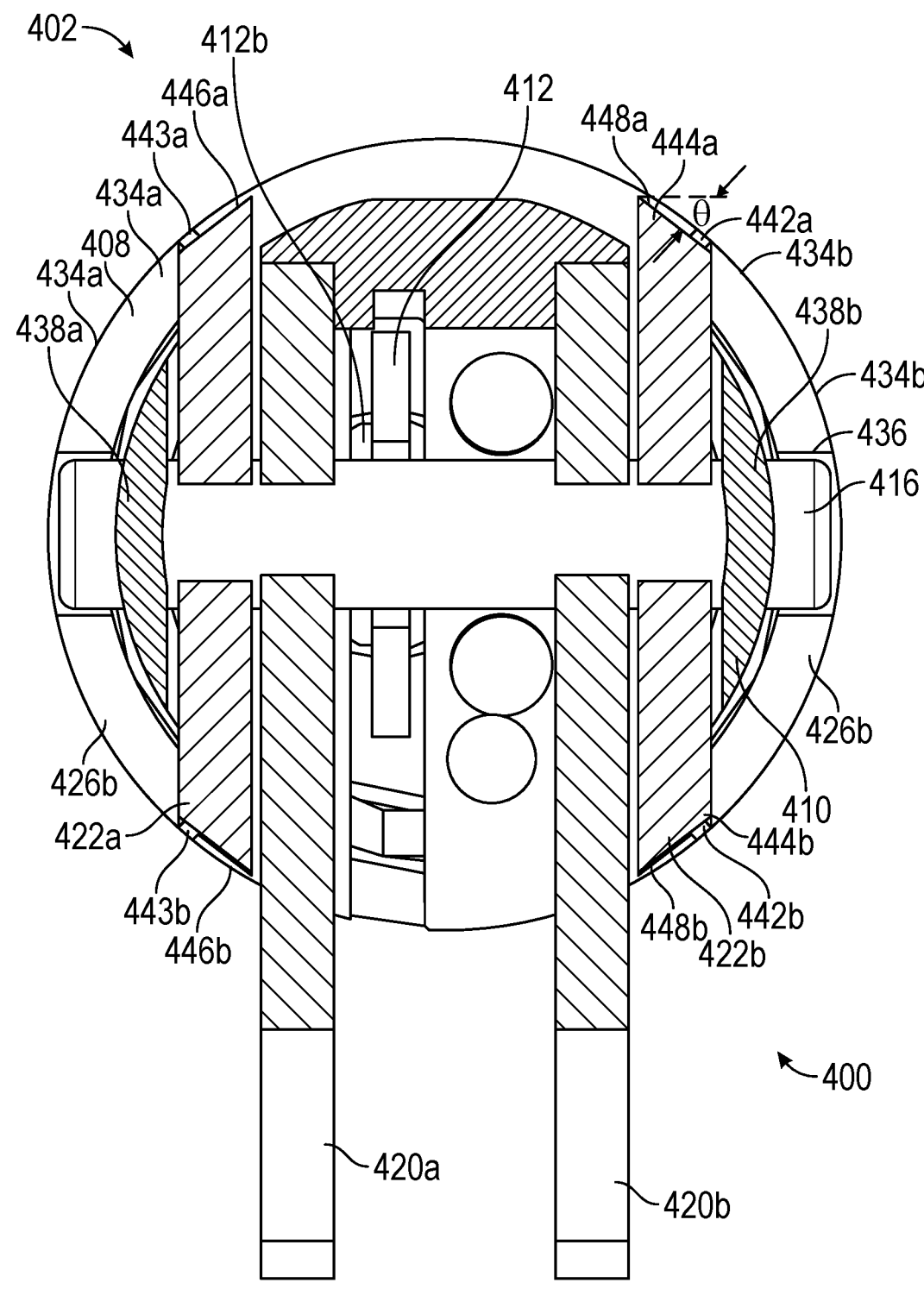
FIG. 5 illustrates a cross-sectional view of a portion of a forceps.

The forceps 200 can include an end effector 202 that can be connected to a handle (such as the handle 104). The end effector 202 can include jaws 206*a* and 206*b*, an outer shaft 208, grip plates 209*a* and 209*b*, an inner shaft 210, a blade assembly 212, a pivot pin 214, a drive pin 216, and a guide pin 218. The jaw 206*a* can include flanges 220*a* and 220*b*, and the jaw 206*b* can include flanges 222*a* and 222*b*. The grip plate 209*a* can include a blade slot 224*a* and the grip plate 209*b* can include a blade slot 224*b*. The blade assembly 212 can include a blade 212*a* and a shaft 212*b* (a similar shaft is shown in FIG. 5). FIGS. 2-3 also show orientation indicators Proximal and Distal and an axis A1.

The components of the forceps 200 can each be comprised of materials such as one or more of metals, plastics, foams, elastomers, ceramics, composites, combinations thereof, or the like. Materials of some components of the forceps 200 are discussed below in further detail. Optionally, the forceps 200 (and those discussed below) can be single-use or disposable forceps. Optionally, the forceps 200 (and those discussed below) can be reusable (e.g., autoclavable or sterilizable) forceps.

The jaws 206*a* and 206*b* can be rigid or semi-rigid members configured to engage tissue. The jaws 206*a* and 206*b* can be coupled to the outer shaft 208, such as pivotably coupled, via the pivot pin 214. The pivot pin 214 can extend through a portion of the jaws 206*a* and 206*b* (such as a bore of each of the jaws 206*a* and 206*b*) such that the pivot pin 214 can be received by outer arms of the outer shaft 208. In other examples, the jaws 206*a* and 206*b* can be pivotably coupled to the outer shaft 208 via a boss or bosses of the outer shaft 208. In another example, the jaws 206*a* and 206*b* can include a boss (or bosses) receivable in bores of the outer shaft 208 to pivotably couple the jaws 206*a* and 206*b* to the outer shaft 208. In another example, outer shaft 208 can include a boss (or bosses) receivable in bores of the jaws 206*a* and 206*b* to pivotably couple the jaws 206*a* and 206*b* to the outer shaft 208.

The flanges 220*a* and 220*b* (which can be a set of flanges, that is, two flanges) can be rigid or semi-rigid members located at a proximal portion of the jaw 206*a*. Similarly, the flanges 222*a* and 222*b* can be rigid or semi-rigid members located at a proximal portion of the jaw 206*b*. In some examples, the flanges 222 can be positioned or located laterally outward of the inner flanges 220.

The grip plates 209*a* and 209*b* of the jaws 206*a* and 206*b* can each be a rigid or semi-rigid member configured to engage tissue and/or the opposing jaw to grasp tissue, such as during an electrosurgical procedure. One or more of the grip plates 209*a* and 209*b* can include one or more of serrations, projections, ridges, or the like configured to increase engagement pressure and friction between the grip plates 209*a* and 209*b* and tissue. The flanges 220 of the upper jaw 206*a* can extend proximally away from the grip plate 209*a* and 209*b*, and in some examples, substantially downward when the upper jaw 206*a* is in the open (e.g., FIG. 3) and partially open positions. The flanges 222 of the lower jaw 206*b* can extend proximally away from the grip plate, such that the jaws 206*a* and 206*b* and flanges 220 and 222 operate to open and close in a scissoring manner.

The jaws 206*a* and 206*b* can each include an electrode configured to deliver electricity or electrosurgical energy to tissue (optionally through the grip plates 209*a* and 209*b*), and a frame supporting the electrode. The blade slots 224*a* and 224*b* of the grip plates 209*a* and 209*b* can together be configured to receive a blade between the jaws 206*a* and 206*b*, such as when the jaws are moved out of the open position. In some examples, only one blade slot can be used.

Each of the inner shaft 210 and the outer shaft 208 can be a rigid or semi-rigid and elongate body having a geometric shape of a cylinder, where the shape of the inner shaft 210 matches or is generally similar to the shape of the outer shaft 208. In some examples, the inner shaft 210 and the outer shaft 208 can have other shapes such as an oval prism, a rectangular prism, a hexagonal prism, an octagonal prism, or the like. In some examples, the shape of the inner shaft 210 can be different from the shape of the outer shaft 208.

The inner shaft 210 can extend substantially proximally to distally along the axis A1, which can be a longitudinal axis. In some examples, the axis A1 can be a central axis. Similarly, the outer shaft 208 can extend substantially proximally to distally along the axis A1. In some examples, the axis A1 can be a central axis of one or more of the inner shaft 210 and the outer shaft 208. The inner shaft 210 can include an axial bore extending along the axis A1. The outer shaft 208 can also include an axial bore extending along the axis A1. The inner shaft 210 can have an outer dimension (such as an outer diameter) smaller than an inner diameter of the outer shaft 208 such that the inner shaft 210 can be positioned within the outer shaft 208 and such that the inner shaft 210 can be translatable in the outer shaft 208 along the axis A1. The inner shaft 210 can also be referred to as a drive shaft 210, a cam shaft 210, or an inner tube 210. The outer shaft 208 can also be referred to as an outer tube 208.

The blade 212a can be an elongate cutting member at a distal portion of the blade assembly 212. The blade 212a can include one or more sharpened edges configured to cut or resect tissue or other items. The blade assembly 212 can be located within the outer shaft 208 (and can be located within the inner shaft 210). The blade 212a can extend along (and optionally parallel with) the axis A1. The blade 212a can be translatable with respect to the inner shaft 210 and the outer shaft 208 to extend between (or into) the first jaw 206a and the second jaw 206b, such as along the blade slots 224a and 224b. In some examples, the blade 212a can extend axially through the inner shaft 210 offset from the axis A1. In some examples, the blade 212a the blade can extend axially through the flanges 220 and 222 such that the blade 212a is in a position laterally inward of the first set of flanges 220 and the second set of flanges 222. The blade 212a can also be a translating member or electrosurgical component other than a blade. For example, the translating member 212a can be an electrode, such as a blunt electrode, a needle electrode, or a snare electrode.

The guide 218, the drive pin 216, and the pivot pin 214 can each be a rigid or semi-rigid pin, such as a cylindrical pin. The guide 218, the drive pin 216, and the pivot pin 214 can have other shapes in other examples, such as rectangular, square, oval, or the like. In some examples, the pivot pin 214 can have a size (such as a diameter) that is larger than the drive pin 216, as discussed below in further detail. Each pin can have a smooth surface to help reduce surface friction between the pins and components of the forceps 200, such as between the pivot pin 214 and the outer shaft 208 or the drive pin 216 and the flanges 220 and 222. Each of the guide 218, the drive pin 216, and the pivot pin 214 can be other components such as one or more projections, bosses, arms, or the like.

In operation, the inner shaft 210 can be translated using an actuator (such as the lever 116 of FIG. 1). The inner shaft 210 can translate with respect to the outer shaft 208 to move the drive pin 216. The drive pin 216 can engage the flanges 220 to move the flanges 220 between open and closed positions, which can cause the jaw 206a to move between open and closed positions with respect to the jaw 206b.

Though the forceps 200 are shown and discussed as being a cutting forceps or a coagulating forceps, the forceps 200 can be various other types of forceps or instruments used for grasping, cutting, measuring, coagulating, or the like.

Figure 4:
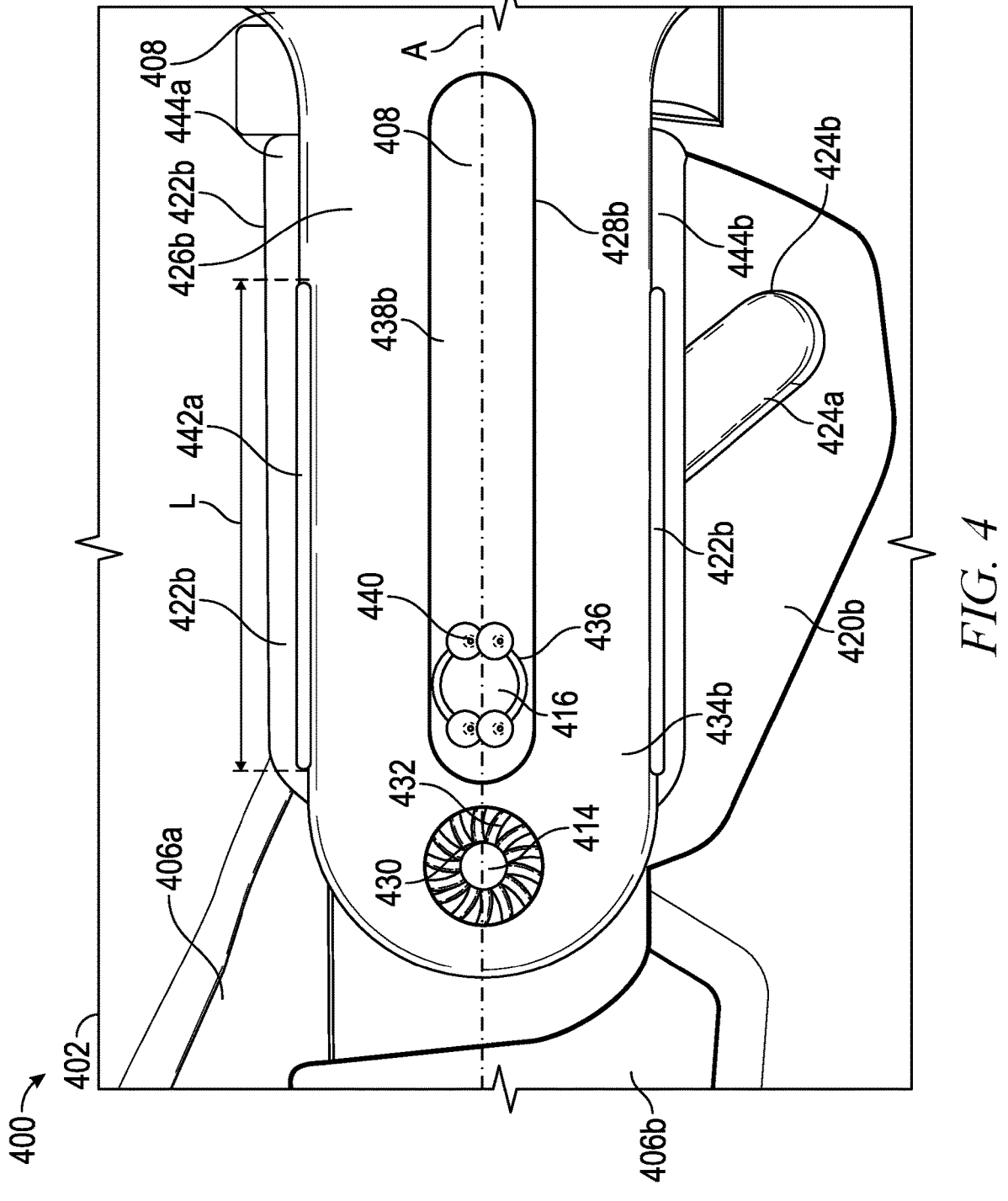
FIG. 4 illustrates a side view of a portion of forceps.

FIG. 4 illustrates a side view of a portion of forceps 400 in an open position. The forceps 400 can be similar to the forceps 200 discussed above. FIG. 4 shows how the forceps

400 can include one or more welds to secure the fixed jaw to the outer shaft. Any of the forceps discussed above or below can include the features of the forceps 400.

The forceps 400 can include an end effector 402, an inner shaft 410, and an outer shaft 408. The end effector 402 can include jaws 406a and 406b (jaws 406), a pivot pin 414, and a cam pin 416. The jaw 406a can include flanges 420a and 420b (flanges 420) and the jaw 406b can include flanges 422a and 422b (flanges 422). The components of the forceps 400 can be connected and can operate similar to the forceps 200.

The flanges 420a and 420b can each include a track 424a and 424b that can each be configured to receive the cam pin 416 therein. During operation, the shaft (such as the inner shaft 410) can be operated to drive the cam pin in the tracks 424a and 424b to cause the flanges 420 to move, causing the jaw 406a to move with respect to the jaw 406b between an open position and a closed position, as discussed above with respect to FIGS. 1-3. The flanges 420a and 420b (flange 420b is only partially visible in FIG. 4) are in the open position in FIG. 4 as the jaw 406a is open with respect to the jaw 406b.

FIG. 4 also shows that the outer shaft 408 can include arms 426a and 426b (collectively referred to as arms 426), which can extend distally and can include a gap therebetween. The arms 426a and 426b can each include a slot 428a and 428b, respectively. The slots 428 can receive the cam pin 416 at least partially therein or therethrough to limit vertical (or lateral or radial) movement of the cam pin 416 with respect to the outer shaft 408, such as to limit movement of the cam pin 416 (and therefore the inner shaft 410 to which the cam pin 416 is connected) to limit axial movement of the cam pin 416 for proper camming interaction of the cam pin 416 and the flanges 420 to operate the jaw 406a.

FIG. 4 also shows that the pivot pin 414 can extend through the arms 426 and can be welded to the arms 426. The pivot pin 414 can extend at least partially through bores 430 of the arms 426. A weld 432, which can be a seam weld or a series of spot welds (e.g., laser spot or tack welds) can be applied to a perimeter of the pivot pin 414 and an outer surface 434 of the arms 426 to fixedly secure the pivot pin 414 to the outer shaft 408.

FIG. 4 also shows that the inner shaft 410 can include arms 438a and 438b (collectively referred to as arms 438), which can extend distally and can include a gap therebetween. FIG. 4 further shows that the cam pin 416 can be welded to the inner shaft 410. The cam pin 416 can extend at least partially through bores 436 of the arms 438. A weld 440, which can be a seam weld or a series of spot welds (e.g., laser spot or tack welds) can be applied to a perimeter of the cam pin 416 and an outer surface of the arms 438. Though four welds (e.g., four spot welds or four tack welds) are shown, 1, 2, 3, 5, 6, 7, 8, 9, 10, 15, or the like welds can be used to secure the cam pin 416 to the arms 438.

FIG. 4 also shows that the end effector 402 can include welds 442a and 442b (welds) applied to upper and lower portions 444a and 444b of the flange 422b and to the arm 426b. The flange 422a can be similarly secured to the arm 426a as discussed with respect to FIG. 5. The welds 442 can extend over at least a portion of the outer surface of the arms 438 and at least a portion of the flanges 422. The welds 442 can extend axially or longitudinally such as to form seam welds. The welds 442 can also be overlapping tack or spot welds, such as laser spot welds or laser tack welds that are overlapping. The flanges 422 can be positioned or located laterally outward of the flanges 420 such as to allow the welds 442 to be applied to the flanges 422 and the outer shaft 408.

The individual welds can have a diameter following application between 0.01 millimeters (mm) and 0.75 mm, such as between 0.10 mm and 0.50 mm, such as between 0.25 mm and 0.45 mm. For example, the individual welds can have a diameter of 0.25 mm, 0.3 mm, or 0.35 mm. The welds 442 can have an axial length L along the axis A or approximately along the axis A, such as laterally outward thereof or such as parallel to the axis A. The length L can be between 1 mm and 10 mm, such as between 2.5 mm and 10.0 mm. For example, one or more of the welds 442 can have a length between 3 mm and 8 mm. For example, one or more of the welds can have a length of 3 mm, 3.5 mm, 4 mm, 4.5 mm, 5 mm, 5.5 mm, 6 mm, 6.5 mm, 7 mm, 7.5 mm, 8 mm, or the like.

FIG. 5 illustrates a cross-sectional view across indicators 5-5 of FIG. 2 of a portion of the forceps 400. The forceps 400 of FIG. 5 can be similar to or the same as the forceps 400 or the forceps 200 discussed above. FIG. 5 shows additional details of the forceps 400.

For example, FIG. 5 shows how or where the welds 442a and 442b can be placed and shows welds 443a and 443b. The welds 442 and 443 can be parallel or can all extend axially or longitudinally. The welds 442a and 442b can be secured, connected, fused to, or formed with the flange 422b and the outer shaft 408, such as to the arm 426b. Similarly, the welds 443a and 443b can be secured, connected, fused to, or formed with the flange 422a and the outer shaft 408, such as to the arm 426a. More specifically, the weld 443a can be fused to a top surface 446a of the flange 422a and to an outer surface 434a of the arm 426a. The weld 443b can be fused to a bottom surface 446b of the flange 422a and to an outer surface 434a of the arm 426a. Also, the weld 442a can be fused to a top surface 448a of the flange 422b and to an outer surface 434b of the arm 426b, and the weld 442b can be fused to a top surface 448b of the flange 422a and to an outer surface 434a of the arm 426a.

Though FIG. 5 shows four welds 442a, 442b, 443a, and 443b, the end effector 402 can include fewer or less welds. For example, the end effector 402 can include only two welds or three welds. For example, when the end effector 402 includes only three welds, one of the four welds 442a, 442b, 443a, and 443b can be omitted. When the end effector 402 includes two welds, the welds can be on the same side, on opposite sides, or across and opposite sides. For example, the end effector 402 can include welds 442a and 442b. In another example, the end effector 402 can include welds 443a and 443b. In another example, the end effector 402 can include welds 442a and 443a. In another example, the end effector 402 can include welds 442b and 443b. In another example, the end effector 402 can include welds 442a and 443b. In another example, the end effector 402 can include welds 442b and 443a.

The surfaces 446 and 448 of the flanges 422a and 422b, respectively, can be chamfers, bevels, or other profiles configured to limit extension of the flanges 422 beyond an outer diameter of the outer shaft 408. For example, the surfaces 446 and 448 of the flanges 422a and 422b can extend from a top portion or edge of an inner portion of each flange and can extend laterally or radially outwards in one direction and radially or laterally towards a center in a second direction such that the surfaces 446 and 448 are sloped or shaped to limit extension beyond the outer shaft 408. For example, an angle θ (as shown in FIG. 5) of each of the surfaces 446 and 448 can be between 30 degrees and 50 degrees. For example, the angle θ can be between 35 degrees and 40 degrees, such as 35 degrees, 37.5 degrees, 40 degrees, or the like.

The surfaces 446 and 448 of the flanges 422a and 422b can also be relatively flat. The flanges 422a and 422b can also be sized such as to form a gap between the each of the surfaces 446 and 448 and respective outer surfaces 434 of the respective arms 426 so that the welds 442 and 443 can form to the flanges 422 and the arms 426 without extending beyond (or limit extension beyond) the outer surface of the outer shaft 408.

FIG. 5 also shows that the outer shaft 408 can be cut or formed such that the inner surface(s) of the outer shaft 408 are parallel to and offset from a radius or diameter of the outer shaft 408 such that the outer shaft 408 forms surfaces that are configured to be parallel to outer surfaces of the flanges 422 so that the flanges 422 and the outer shaft 408 can mate or engage to limit any gaps between the outer shaft 408 and the flanges 422 to help provide a secure connection between the flanges 422 and the outer shaft 408 once the welds 442 and the welds 443 are applied or added.

Figure 6:
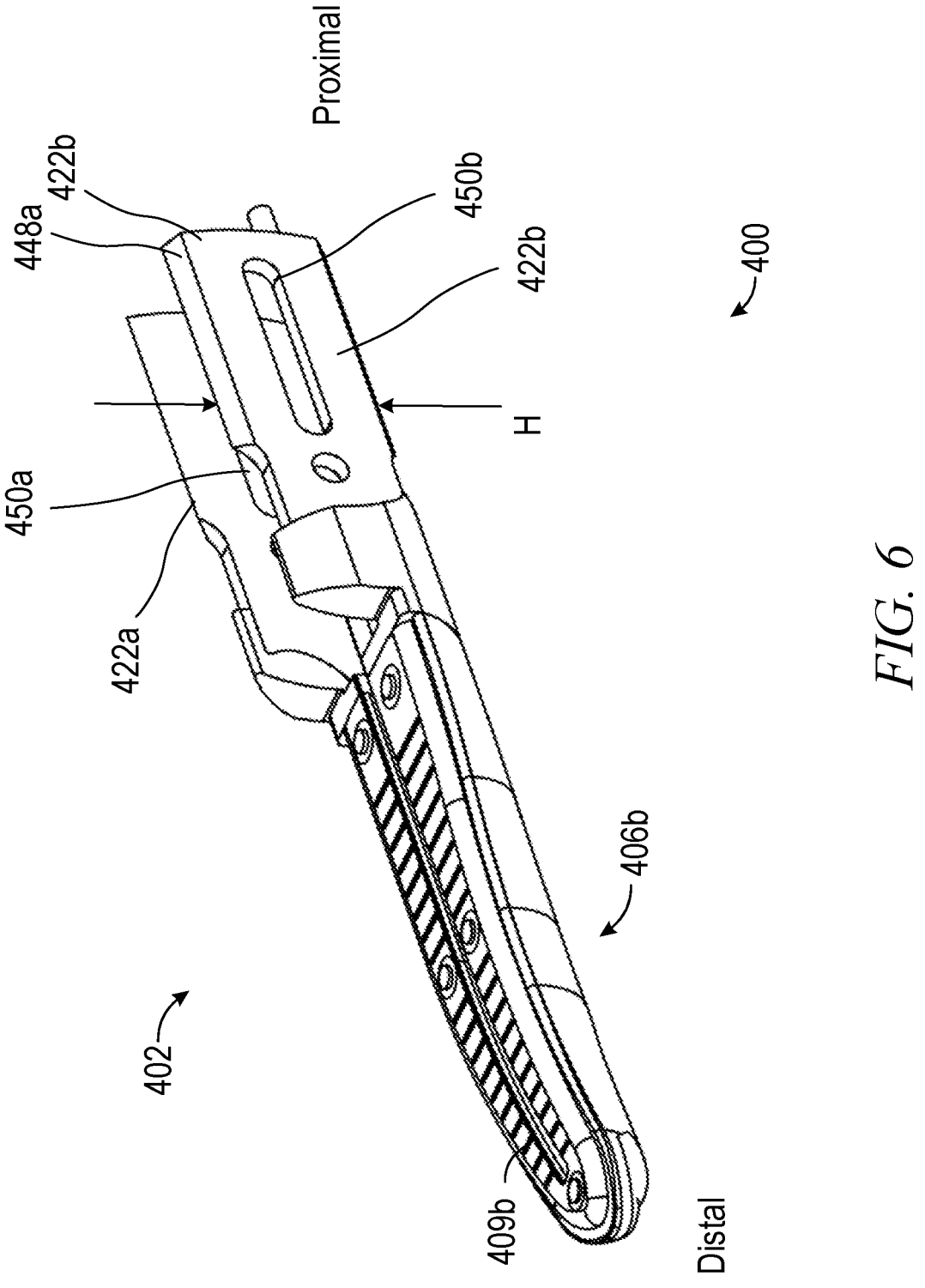
FIG. 6 illustrates an isometric view of a portion of a forceps.

FIG. 6 shows an isometric view of the forceps 400, particularly of the jaw 406b of the end effector 402. The jaw 406b can be consistent with the description of the forceps 200 (or forceps 100) above. FIG. 6 shows how the flanges 422a and 422b can include a fixed track 450a and 450b (collectively referred to as fixed track or tracks 450), respectively, that can be sized and shaped similar to the slots 428. The fixed track 450 can also align or substantially align with the slots 428 of the outer shaft 408. The fixed track 450 can be configured to receive the cam pin 416 at least partially therein or therethrough and can be configured to guide and limit movement of the cam pin 416 along the fixed track 450 and the tracks 424a and 424b.

FIG. 6 also shows that the flanges 422a and 422b can be relatively straight, such that the flanges 422 can align with the outer arms 426 (respectively) to help ensure the surfaces 448 align with the outer shaft 408 to receive the welds. FIG. 6 also shows that the flanges 422a and 422b can each have, include, or define a height H. The height H can be larger or taller than a height of the outer arms 426 and can be larger or taller than the arms 438a and 438b. The flanges 420 can also have a height that is higher or larger than a height of the outer arms 426 and can be larger or taller than the arms 438a and 438b.

NOTES AND EXAMPLES

The following, non-limiting examples, detail certain aspects of the present subject matter to solve the challenges and provide the benefits discussed herein, among others.

Example 1 is a surgical forceps comprising: an outer shaft; a first jaw including a first flange and a second flange, the first jaw pivotably coupled to the outer shaft; a second jaw including a third flange and a fourth flange, the third flange welded to the outer shaft and the fourth flange welded to the outer shaft; and an inner shaft engaged with the first flange and the second flange and the inner shaft movable with respect to the outer shaft, the third flange, and the fourth flange to move the first jaw between an open position and a closed position.

In Example 2, the subject matter of Example 1 optionally includes wherein the outer shaft includes a first outer arm and a second outer arm, wherein the surgical forceps includes a pivot pin extending through the first flange and the second flange, and wherein the pivot pin is welded to each of the first outer arm and the second outer arm.

In Example 3, the subject matter of Example 2 optionally includes wherein the third flange is welded to the first outer arm and wherein the fourth flange is welded to the second outer arm.

In Example 4, the subject matter of Example 3 optionally includes wherein the inner shaft includes a first inner arm and a second inner arm located laterally inward of the first outer arm and the second outer arm, wherein the surgical forceps includes a cam pin welded to each of the inner arms, wherein the first flange and the second flange define, respectively, a first track and a second track, and wherein the inner shaft is movable to move the cam pin along the first track and the second track to move the first jaw between the open position and the closed position.

In Example 5, the subject matter of Example 4 optionally includes wherein the third flange is welded to the first outer arm along a top portion of the first outer arm and along a bottom portion of the first outer arm, and wherein the fourth flange is welded to the second outer arm along a top portion of the second outer arm and along a bottom portion of the second outer arm.

In Example 6, the subject matter of Example 5 optionally includes wherein the top portion of the third flange includes a bevel configured to form a gap between the bevel and an outer surface of the first outer arm, the gap configured to receive a first seam weld to limit extension of the first seam weld beyond the outer surface of the first outer arm.

In Example 7, the subject matter of Example 6 optionally includes wherein third flange and the fourth flange each have a height that is larger than a height of the first outer arm and the second outer arm and is larger than a height of the first inner arm and the second inner arm.

In Example 8, the subject matter of any one or more of Examples 3-7 optionally include wherein the third flange is welded to the first outer arm by a first seam weld and wherein the fourth flange is welded to the second outer arm by a second seam weld.

In Example 9, the subject matter of Example 8 optionally includes wherein a length of the first seam weld or the second seam weld is between 2.5 millimeters and 7.5 millimeters.

In Example 10, the subject matter of Example 9 optionally includes wherein the first seam weld is a laser seam weld comprised of individual laser spots each having a diameter between 0.05 millimeters and 0.25 millimeters.

Example 11 is a surgical forceps comprising: an outer shaft; a cam pin; a first jaw including a first flange and a second flange, the first jaw pivotably coupled to the outer shaft, and the cam pin extending at least partially through the first flange and the second flange; a second jaw including a third flange and a fourth flange, the third flange and the fourth flange each welded to the outer shaft; and an inner shaft connected to the cam pin, the inner shaft movable with respect to the outer shaft, the third flange, and the fourth flange to move the cam pin along the first flange and the second flange to move the first jaw between an open position and a closed position.

In Example 12, the subject matter of Example 11 optionally includes wherein the outer shaft includes a first outer arm and a second outer arm, wherein the surgical forceps includes a pivot pin welded to each of the first outer arm and the second outer arm.

In Example 13, the subject matter of Example 12 optionally includes wherein the third flange is welded to the first outer arm and wherein the fourth flange is welded to the second outer arm.

In Example 14, the subject matter of Example 13 optionally includes wherein the cam pin is welded to the inner shaft.

In Example 15, the subject matter of any one or more of Examples 13-14 optionally include wherein the third flange and the fourth flange each have a height that is larger than a height of the first outer arm and the second outer arm.

In Example 16, the subject matter of Example 15 optionally includes wherein the third flange is welded to the first outer arm along a top portion of the first outer arm and along a bottom portion of the first outer arm, and wherein the fourth flange is welded to the second outer arm along a top portion of the second outer arm and along a bottom portion of the second outer arm.

In Example 17, the subject matter of Example 16 optionally includes wherein the top portion of the third flange includes a bevel configured to form a gap between the bevel and an outer surface of the first outer arm, the gap configured to receive a first seam weld to weld the bevel to the top portion of the first outer arm and to limit extension of the first seam weld beyond the outer surface of the first outer arm.

In Example 18, the subject matter of Example 17 optionally includes wherein the first seam weld extends longitudinally or axially, and wherein the second seam weld extends longitudinally or axially.

In Example 19, the subject matter of any one or more of Examples 12-18 optionally include wherein inner shaft includes a pair of inner arms located laterally inward of the first outer arm and the second outer arm, the cam pin welded to each of the inner arms, wherein the first flange and the second flange define, respectively, a first track and a second track, and wherein the inner shaft is movable to move the cam pin along the first track and the second track to move the first jaw between the open position and the closed position.

In Example 20, the subject matter of Example 19 optionally includes wherein the third flange includes a third track and the fourth flange includes a fourth track, the cam pin extending at least partially through the third track and the fourth track, and the cam pin movable along the third track and the fourth track.

In Example 21, the subject matter of Example 20 optionally includes wherein first track and the second track are curved to allow the first jaw to move between the open position and the closed position with respect to the second jaw, and wherein the third track and the fourth track are straight.

In Example 22, the subject matter of any one or more of Examples 11-21 optionally include wherein the first flange and the second flange are located laterally inward of the third flange and the fourth flange.

In Example 23, the apparatuses or method of any one or any combination of Examples 1-22 can optionally be configured such that all elements or options recited are available to use or select from.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The invention claimed is:

1. A surgical forceps comprising:
an outer shaft comprising a first outer arm and a second outer arm;
a first jaw including a first flange and a second flange, the first jaw pivotably coupled to the outer shaft;
a pivot pin extending through the first flange and the second flange, wherein the pivot pin is welded to each of the first outer arm and the second outer arm;
a second jaw including a third flange and a fourth flange, the third flange welded to the first outer arm of the outer shaft and the fourth flange welded to the second outer arm of the outer shaft, a top portion of the third flange including a bevel configured to form a gap between the bevel and an outer surface of the first outer arm, a first seam weld connected to the bevel and the outer surface at the gap to limit extension of the first seam weld beyond the outer surface of the first outer arm; and
an inner shaft engaged with the first flange and the second flange and the inner shaft movable with respect to the outer shaft, the third flange, and the fourth flange to move the first jaw between an open position and a closed position.

2. The surgical forceps of claim 1 wherein the inner shaft includes a first inner arm and a second inner arm located laterally inward of the first outer arm and the second outer arm, wherein the surgical forceps includes a cam pin welded to each of the first inner arm and the second inner arm, wherein the first flange and the second flange define, respectively, a first track and a second track, and wherein the inner shaft is movable to move the cam pin along the first track and the second track to move the first jaw between the open position and the closed position.

3. The surgical forceps of claim 2, wherein the third flange is welded to the first outer arm along a top portion of the first outer arm and along a bottom portion of the first outer arm, and wherein the fourth flange is welded to the second outer arm along a top portion of the second outer arm and along a bottom portion of the second outer arm.

4. The surgical forceps of claim 3, wherein third flange and the fourth flange each have a height that is larger than a height of the first outer arm and the second outer arm and is larger than a height of the first inner arm and the second inner arm.

5. The surgical forceps of claim 1, wherein the fourth flange is welded to the second outer arm by a second seam weld.

6. The surgical forceps of claim 5, wherein a length of the first seam weld or the second seam weld is between 2.5 millimeters and 7.5 millimeters.

7. The surgical forceps of claim 6, wherein the first seam weld is a laser seam weld comprised of individual laser spots each having a diameter between 0.05 millimeters and 0.25 millimeters.

8. A surgical forceps comprising:
an outer shaft comprising a first outer arm and a second outer arm;
a pivot pin welded to each of the first outer arm and the second outer arm;
a cam pin;
a first jaw including a first flange and a second flange, the first jaw pivotably coupled to the outer shaft, and the cam pin extending at least partially through the first flange and the second flange;
a second jaw including a third flange and a fourth flange, the third flange welded to the first outer arm of the outer shaft and the fourth flange welded to the second outer arm of the outer shaft; and
an inner shaft connected to the cam pin, the inner shaft movable with respect to the outer shaft, the third flange, and the fourth flange to move the cam pin along the first flange and the second flange to move the first jaw between an open position and a closed position;
wherein a top portion of the third flange includes a bevel configured to form a gap between the bevel and an outer surface of the first outer arm, a first seam weld connected to the bevel and the outer surface at the gap to limit extension of the first seam weld beyond the outer surface of the first outer arm.

9. The surgical forceps of claim 8, wherein the cam pin is welded to the inner shaft.

10. The surgical forceps of claim 8, wherein the third flange and the fourth flange each have a height that is larger than a height of the first outer arm and the second outer arm.

11. The surgical forceps of claim 10, wherein the third flange is welded to the first outer arm along a top portion of the first outer arm and along a bottom portion of the first outer arm, and wherein the fourth flange is welded to the second outer arm along a top portion of the second outer arm and along a bottom portion of the second outer arm.

12. The surgical forceps of claim 11, wherein the first seam weld extends longitudinally or axially.

13. The surgical forceps of claim 8, wherein the inner shaft includes a pair of inner arms located laterally inward of the first outer arm and the second outer arm, the cam pin welded to each of the inner arms, wherein the first flange and the second flange define, respectively, a first track and a second track, and wherein the inner shaft is movable to move the cam pin along the first track and the second track to move the first jaw between the open position and the closed position.

14. The surgical forceps of claim 13, wherein the third flange includes a third track and the fourth flange includes a fourth track, the cam pin extending at least partially through the third track and the fourth track, and the cam pin movable along the third track and the fourth track.

15. The surgical forceps of claim 14, wherein first track and the second track are curved to allow the first jaw to move between the open position and the closed position with respect to the second jaw, and wherein the third track and the fourth track are straight.

16. The surgical forceps of claim 8, wherein the first flange and the second flange are located laterally inward of the third flange and the fourth flange.

17. A surgical forceps comprising:
an outer shaft comprising:
    a first outer arm including an outer surface; and
    a second outer arm;

a pivot pin welded to each of the first outer arm and the second outer arm;
a cam pin;
a first jaw including a first flange and a second flange, the first jaw pivotably coupled to the outer shaft, and the cam pin extending at least partially through the first flange and the second flange;
a second jaw including a third flange and a fourth flange, the fourth flange welded to the second outer arm of the outer shaft, and the third flange including a top portion including a bevel forming a gap between the bevel and the outer surface of the first outer arm;
a first seam weld connected to the bevel and the outer surface at the gap to limit extension of the first seam weld beyond the outer surface of the first outer arm; and
an inner shaft connected to the cam pin, the inner shaft movable with respect to the outer shaft, the third flange, and the fourth flange to move the cam pin along the first flange and the second flange to move the first jaw between an open position and a closed position.

* * * * *